United States Patent
Baloglu

(10) Patent No.: US 7,186,851 B2
(45) Date of Patent: Mar. 6, 2007

(54) FACILE METHOD FOR SYNTHESIZING BACCATIN III COMPOUNDS

(75) Inventor: Erkan Baloglu, Stoneham, MA (US)

(73) Assignee: Immunogen, Inc., Cambridge, MA (US)

( * ) Notice: Subject to any disclaimer, the term of this patent is extended or adjusted under 35 U.S.C. 154(b) by 0 days.

(21) Appl. No.: 11/127,234

(22) Filed: May 12, 2005

(65) Prior Publication Data

US 2005/0256323 A1 Nov. 17, 2005

Related U.S. Application Data

(60) Provisional application No. 60/570,834, filed on May 14, 2004.

(51) Int. Cl.
*C07D 305/00* (2006.01)
*C07D 407/00* (2006.01)
*C07D 493/00* (2006.01)

(52) U.S. Cl. .................................. 549/510
(58) Field of Classification Search ............... 514/471, 514/337, 444, 449; 549/60, 473, 510, 511
See application file for complete search history.

(56) References Cited

U.S. PATENT DOCUMENTS 6,706,896 B1 3/2004 Holton et al.

FOREIGN PATENT DOCUMENTS

WO 99/09021 * 2/1999

OTHER PUBLICATIONS

Holton et al., Tetrahedron Letters, "selective Protection of the C(7) and C(10) Hydroxyl Groups in 10-Deacetyl Baccatin III", vol. 39, pp. 2883-2886.*
Damen et al., Herba Polonica, "Direct conversion of 10-Deacetylbaccatin III into baccatin III as a useful synthetic tool for a high yield paclitaxel semisynthesis", vol. 44, pp. 238-242.*
International Search Report and Written Opinion dated Sep. 19, 2005.

* cited by examiner

*Primary Examiner*—Margaret D. Seaman
*Assistant Examiner*—Niloofar Rahmani
(74) *Attorney, Agent, or Firm*—Sughrue Mion, PLLC

(57) ABSTRACT

A process for synthesizing a C-7 protected baccatin III compound represented by formula (A), which comprises reacting a 10-deacetylbaccatin III compound represented by formula (B) with a protecting agent and an acylating agent in the presence of a secondary amine and a nitrogen-containing compound. Also, a process for synthesizing a C-7 protected 10-deacetylbaccatin III compound represented by formula (C), which comprises reacting a 10-deacetylbaccatin III compound represented by formula (B) with a protecting agent in the presence of a secondary amine and a nitrogen-containing compound. In both processes the nitrogen-containing compound is selected from a nitrogen-containing heterocycle or a trialkylamine. When the nitrogen-containing heterocycle is selected, it may be an unsubstituted or a substituted pyridine or an unsubstituted or a substituted pyrazine. When a trialkylamine is selected, it may be, for example, triethylamine or diisopropylethylamine.

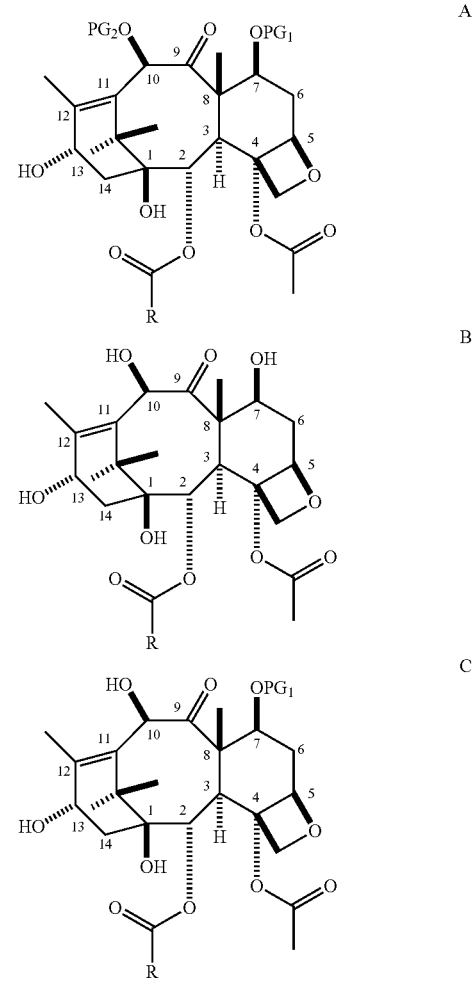

wherein $PG_1$ represents the organic residue of the protecting agent, $PG_2$ represents the organic residue of the acylating agent, and R represents a simple or substituted aryl group or a heterocyclic group.

69 Claims, 6 Drawing Sheets

Figure. 3. Conversion of 10-deacetylbaccatin III compunds (3a-d) into 7-triethylsilylbaccatin III compounds (5a-d)
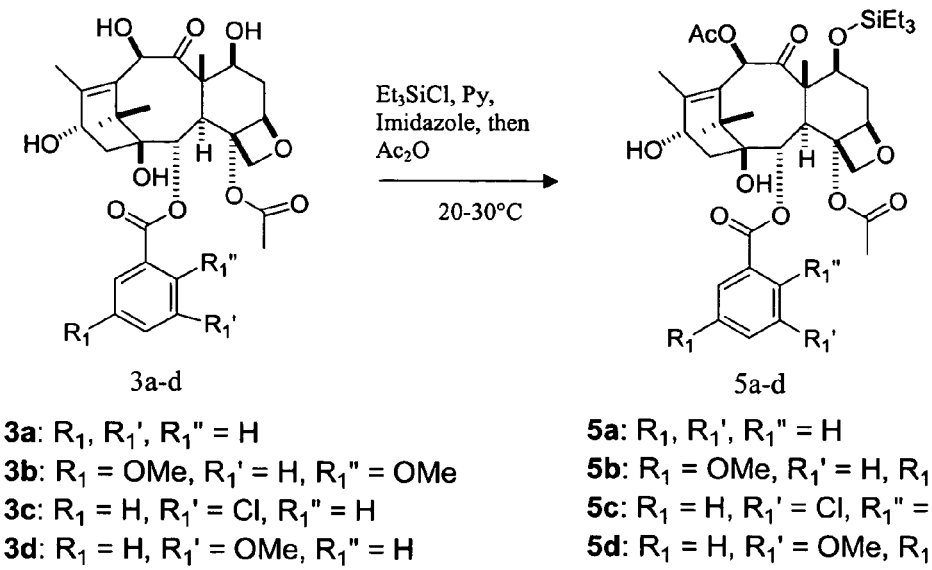
3a-d
3a: $R_1, R_1', R_1'' = H$
3b: $R_1 = OMe, R_1' = H, R_1'' = OMe$
3c: $R_1 = H, R_1' = Cl, R_1'' = H$
3d: $R_1 = H, R_1' = OMe, R_1'' = H$
5a-d
5a: $R_1, R_1', R_1'' = H$
5b: $R_1 = OMe, R_1' = H, R_1'' = OMe$
5c: $R_1 = H, R_1' = Cl, R_1'' = H$
5d: $R_1 = H, R_1' = OMe, R_1'' = H$ Figure 4a. Synthesis of 7-triethylsilyl-2-debenzoyl-2-(2-thiophenoyl)baccatin III (7)
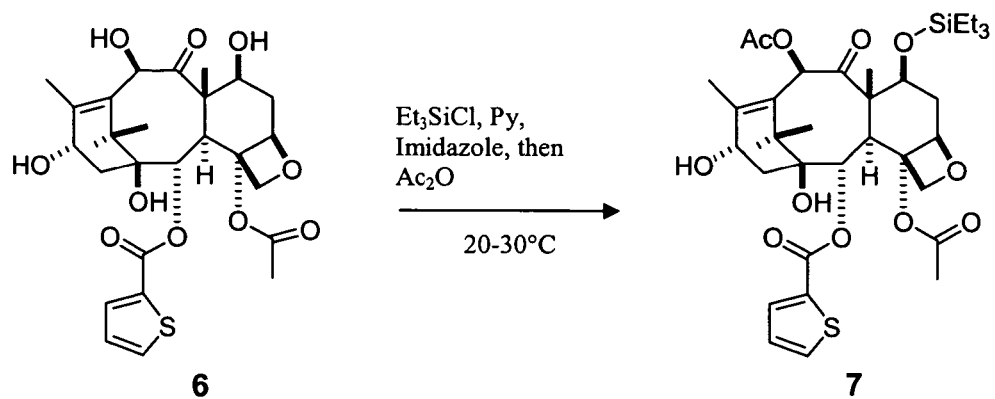
Figure 4b. Synthesis of 7-triethylsilyl-2-debenzoyl-2-(3-furoyl)baccatin III (9)
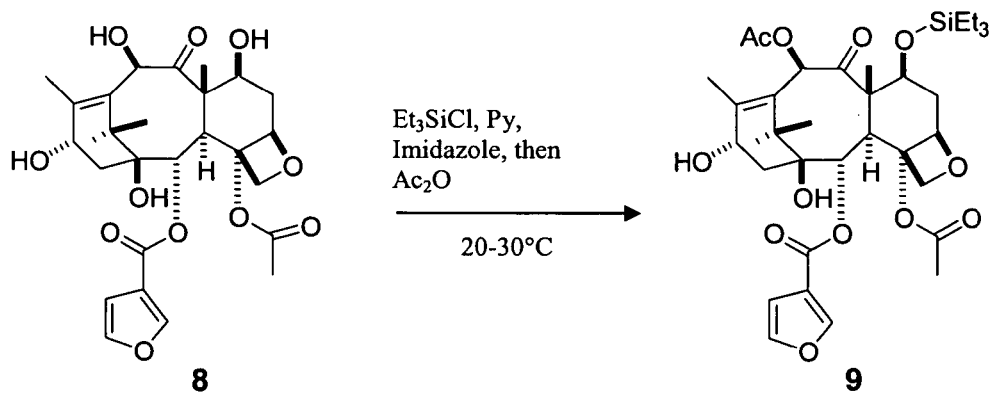

Figure 5. Conversion of 10-deacetylbaccatin III and derivatives (3a-d) to 7-triethylsilyl-10-deacetylbaccatin III and its derivatives (3e-h)
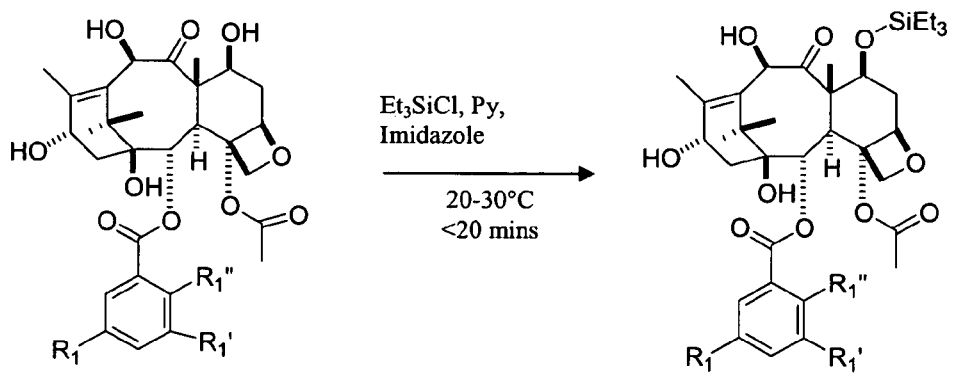
3a: $R_1$, $R_1'$, $R_1''$ = H
3b: $R_1$ = OMe, $R_1'$ = H, $R_1''$ = OMe
3c: $R_1$ = H, $R_1'$ = Cl, $R_1''$ = H
3d: $R_1$ = H, $R_1'$ = OMe, $R_1''$ = H
3e: $R_1$, $R_1'$, $R_1''$ = H
3f: $R_1$ = OMe, $R_1'$ = H, $R_1''$ = OMe
3g: $R_1$ = H, $R_1'$ = Cl, $R_1''$ = H
3h: $R_1$ = H, $R_1'$ = OMe, $R_1''$ = H Figure 6a. Synthesis of 7-triethylsilyl-2-debenzoyl-2-(2-thiophenoyl)-10-deacetylbaccatin III (7a)
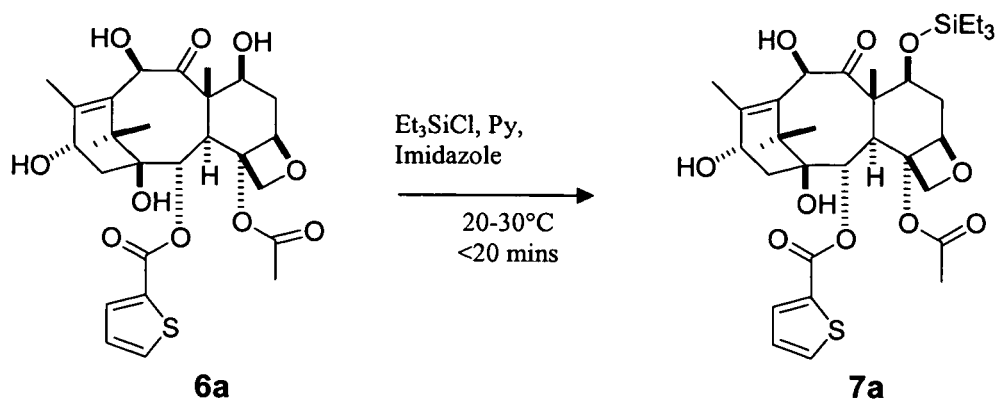
Figure 6b. Synthesis of 7-triethylsilyl-2-debenzoyl-2-(3-furoyl)-10-deacetylbaccatin III (9a)
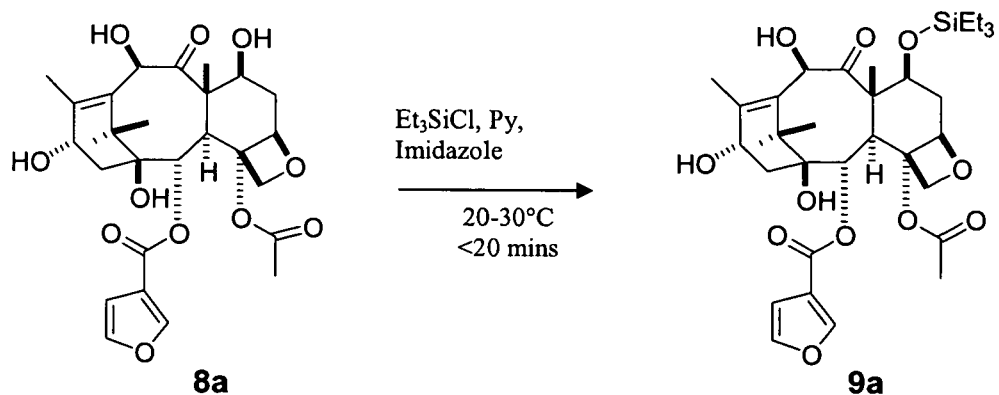

FACILE METHOD FOR SYNTHESIZING BACCATIN III COMPOUNDS

This application claims the benefit of U.S. Provisional Application No. 60/570,834, filed May 14, 2004, the entire disclosure of which is expressly incorporated herein by reference.

FIELD OF THE INVENTION

The present invention relates to a process for the synthesis of baccatin III compounds. These compounds are useful precursors for the synthesis of taxoids. The present invention also relates to a process for the synthesis of an intermediate to the baccatin III compounds.

BACKGROUND OF THE INVENTION

The taxane diterpenoids, or taxoids, are of great interest because of the potent anti-tumor activities of two members of this family, the natural product paclitaxel (Taxol™, 1), and its semi-synthetic analog docetaxel (Taxotere™, 2).

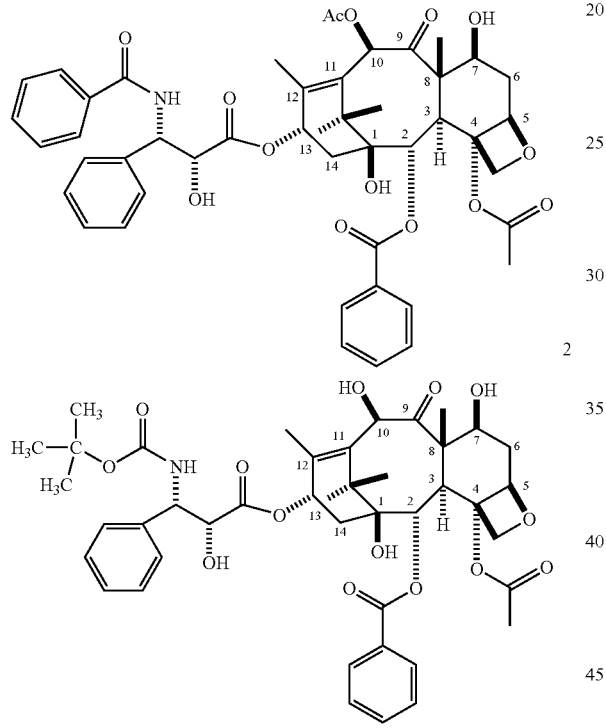

Paclitaxel was first isolated from the bark of the pacific yew tree (*Taxus brevifolia*), in very low yields. Subsequently, a semi-synthetic route to paclitaxel from the more readily available natural product, 10-deacetylbaccatin III (3) was reported.

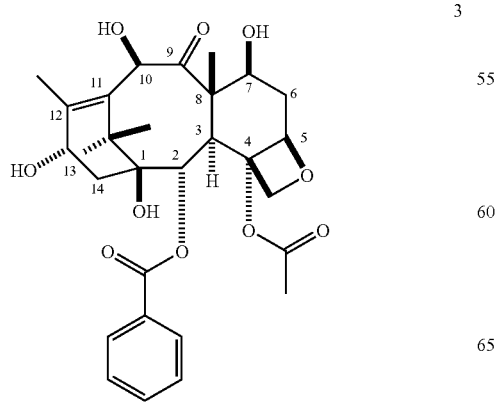

For the synthesis of taxoids, the C-13 side chain is synthesized separately and coupled to the suitably modified baccatin, namely, derivatives of 10-deacetylbaccatin III (3), where the C-7 and the C-10 hydroxyl groups are selectively protected, such that the only location for coupling would be through the C-13 hydroxyl group. The protecting group used for the C-7 hydroxyl group is usually a triethylsilyl (TES) group, while the C-10 position is protected as its acetate ester to give 7-triethylsilylbaccatin III (5).

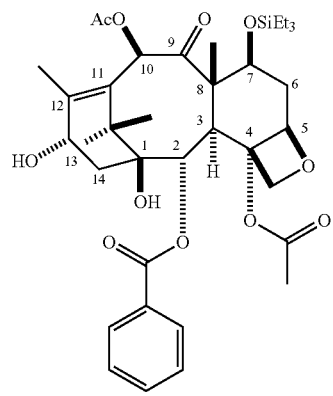

In 10-deacetylbaccatin III (3), the sterically hindered tertiary C-1 hydroxyl group is least reactive, followed by the C-13 hydroxyl group. The C-7 hydroxyl group is easier to access and hence more reactive than the C-10 hydroxyl group.

As a result of the higher reactivity of the hydroxyl group at the C-7 position, attempts for the conversion of 10-deacetylbaccatin III (3) to baccatin III (4) or 7-triethylsilylbaccatin III (5) have been directed to the protection of the hydroxyl group at the C-7 position first, usually in the form of its triethylsilyl ether, as reported in Denis et al (*J. Am. Chem. Soc.,* 1988, 110, 5917). This was followed by acylation at the C-10 position. According to this report, an excess amount of chlorotriethylsilane and pyridine were used. The reaction time was 20 hours for protection of the C-7 hydroxyl as its triethylsilyl ether, and 48 hours for protection of the C-10 hydroxyl as its acetate ester.

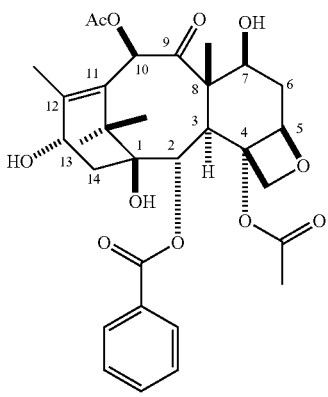

A similar method was reported by Bastart et al. (WO 95/26967), except this time a lower temperature (5° C.) and even longer reaction time (40 hours) were reported for the protection of the C-7 hydroxyl as its triethylsilyl ether, and 48 hours was reported for the acylation of the C-10 hydroxyl.

Another 2-step method (US2002/0087013 A1) uses chlorotriethylsilane and imidazole in dimethylformamide at 0° C., in the first step to form the triethylsilyl ether followed by chromatographic purification. The next acetylation step is conducted at −40° C., followed by another chromatographic purification to give 7-triethylsilylbaccatin III (5).

Alternative methods for the production of 7-triethylsilyl-baccatin III (5) were also reported by Sisti et al, (U.S. Pat. No. 5,914,411) and Holton et al (*Tetrahedron Lett.*, 1998, 39, 2883). In these procedures, the C-10 position is first selectively acylated, followed by protection of the C-7 hydroxyl. However, these methods have several disadvantages including: a) requiring two steps with purifications after each step, b) longer reaction time, and c) potential of undesired incorporation of triethylsilyl groups simultaneously at both the C-7 and C-10 positions.

Thus, all the methods for the incorporation of appropriate protecting groups at the C-7 and C-10 positions of 10-deacetylbaccatin III (3), described thus far, involve long reaction times, use of excess reagents, strictly controlled temperatures, or multiple reaction and purification steps, and potential generation of undesired side products, making the process cumbersome and expensive for scaling up.

SUMMARY OF THE INVENTION

Accordingly, one object of this invention is to provide a new, useful, scalable and inexpensive method for the conversion of a 10-deacetylbaccatin III compound represented by formula (B) to a C-7 protected baccatin III compound represented by formula (A), which can be readily used in commercial processes for the semi-synthesis of paclitaxel, docetaxel and other taxoids. Other taxoids include those containing various R groups comprising substituted phenyl or heterocycles. Such R groups are known to one of skill in the art and can be found, for example, in U.S. Pat. Nos. 5,728,725 and 6,340,701, the disclosures of which are expressly incorporated herein by reference.

Another object of this invention is to provide a new, useful, scalable and inexpensive method for the conversion of 10-deacetylbaccatin III compound represented by formula (B) to a C-7 protected 10-deacetylbaccatin III compound represented by formula (C) which may in turn be converted to a C-7 protected baccatin III compound represented by formula (A).

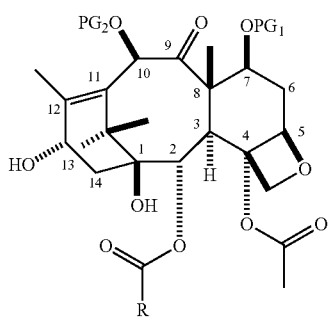

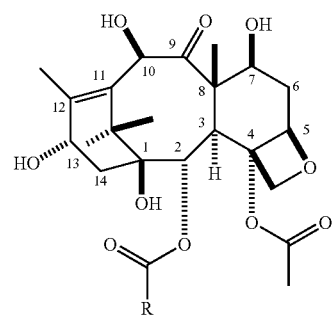

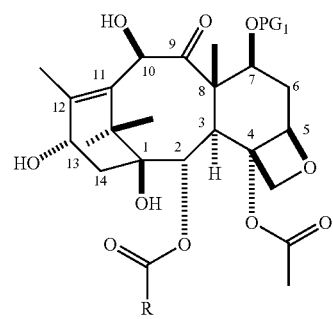

These and other objects have been achieved by providing a process for synthesizing a C-7 protected baccatin III compound represented by formula (A) comprising reacting a 10-deacetylbaccatin III compound represented by formula (B) with a protecting agent and an acylating agent in the presence of a secondary amine and a nitrogen-containing compound. The nitrogen-containing compound is selected from a nitrogen-containing heterocycle or a trialkylamine as described more fully below.

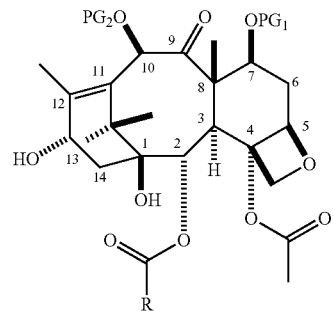

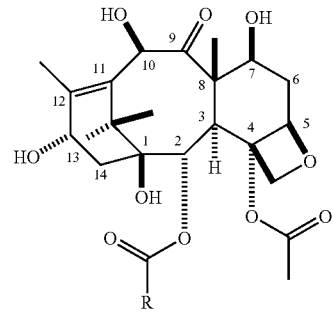

wherein $PG_1$ represents the organic residue of the protecting agent, $PG_2$ represents the organic residue of the acylating agent, and R represents a simple or substituted aryl group or a heterocyclic group.

Preferably, the aryl group represented by R is a group represented by the following formula:

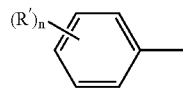

wherein R's may be the same or different and each represents H, an electron withdrawing group or an electron donating group, and n represents 0, or an integer of from 1 to 3. More preferably, the aryl group is phenyl or substituted phenyl.

Preferably, the electron withdrawing group represented by R' is selected from the group consisting of —F, —NO$_2$, —CN, —Cl, —CHF$_2$ and —CF$_3$, and the electron donating group represented by R' is selected from the group consisting of —NR$_7$R$_8$ and —OR$_9$, wherein R$_7$ and R$_8$ are the same or different and each represents a linear alkyl group having 1 to 10 carbon atoms, a branched or cyclic alkyl group having 3 to 10 carbon atoms, or an unsubstituted or substituted aryl group having 6 to 10 carbon atoms, and R$_9$ represents a linear alkyl group having 1 to 10 carbon atoms, or a branched or cyclic alkyl group having 3 to 10 carbon atoms.

R$_7$ and R$_8$ are preferably the same or different and each represents a linear alkyl group having 1 to 4 carbon atoms, or a branched or cyclic alkyl group having 3 to 4 carbon atoms. It is also preferred that R$_7$ and R$_8$ are the same and represent a linear alkyl group having 1 to 10 carbon atoms, a branched or cyclic alkyl group having 3 to 10 carbon atoms, or an unsubstituted or substituted aryl group having 6 to 10 carbon atoms. Further, more preferably, the substituent —NR$_7$R$_8$ is selected from the group consisting of dimethyl amino, diethyl amino, dipropyl amino and dibutyl amino, wherein the propyl moiety represents normal-propyl or isopropyl, and the butyl moiety represents normal-butyl, secondary butyl, tertiary butyl or isobutyl. More preferably, R' is —OCH$_3$ or a chloro.

The aryl group represented by R is preferably phenyl or substituted phenyl, such as methoxyphenyl, dimethoxyphenyl, or chlorophenyl, and more preferably, is represented by the following formulae:

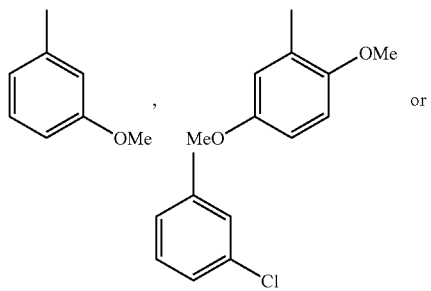

The heterocyclic group represented by R is a 3 to 7 membered ring having 1 to 2 hetero atoms selected from the group consisting of oxygen, nitrogen and sulfur. Examples include furyl, dihydrofuryl, tetrahydrofuryl, pyrollyl, pyrrolidinyl, thienyl, thiazolyl, imidazolyl, pyridyl, morpholinyl, piperidinyl, piperazinyl and oxazolyl. Preferably, the heterocylic group represented by R is furyl or thienyl. More preferably, the heterocyclic group represented by R is represented by the following formula:

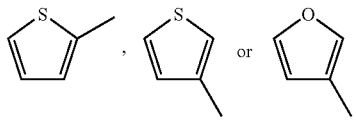

$PG_1$ is preferably trialkylsilyl. $PG_2$ is preferably acyl. More preferably, $PG_1$ is triethylsilyl and $PG_2$ is acetyl. The alkyl group is the same or different and is selected from methyl, ethyl, propyl or butyl, wherein the propyl moiety represents normal-propyl or isopropyl, and the butyl moiety represents normal-butyl, secondary butyl, tertiary butyl or isobutyl.

In the present invention, the protecting agent is preferably an organosilane compound and more preferably, an organosilane compound represented by the formula $(R'')_3SiX$, wherein R''s may be the same or different, and each independently represents methyl, ethyl, normal-propyl, isopropyl, n-butyl, sec-butyl, isobutyl or tert-butyl, and X represents a leaving group. Preferably, the leaving group represented by X is a halogen atom, tosylate, mesylate, or trifluoromethanesulfonate. Most preferably, the protecting agent is chlorotriethylsilane.

In the present invention, the acylating agent is preferably selected from the group consisting of acyl halides and acyl anhydrides. More preferably, the acylating agent is selected from the group consisting of acetyl chloride and acetic anhydride. Most preferably, the acylating agent is acetic anhydride.

In the present invention, the secondary amine is preferably selected from the group consisting of imidazole or substituted imidazoles, and more preferably imidazole.

In the present invention, the nitrogen-containing compound is preferably anhydrous and is also preferably selected from a trialkylamine or a nitrogen-containing heterocycle, preferably pyridine.

Examples of suitable trialkylamines include trimethylamine, triethylamine, diisopropylethylamine, tri-n-propylamine and tri-n-butylamine.

Examples of suitable nitrogen-containing heterocycles include unsubstituted or substituted pyridine such as 2-picoline, 3-picoline and 4-picoline and unsubstituted or substituted pyrazine, such as methylpyrazine.

According to the present invention, the amount of the protecting agent is preferably about 2 equivalents based on the amount of the 10-deacetylbaccatin III compound represented by formula (B). The amount of the acylating agent is preferably in a range of from about 1 to about 20 equivalents based on the amount of the 10-deacetylbaccatin III compound represented by formula (B). The amount of the secondary amine is preferably about 2 to about 6 equivalents based on the amount of the 10-deacetylbaccatin III compound represented by formula (B). The amount of the nitrogen-containing compound is preferably about 0.5 mL per 0.1 g of the 10-deacetylbaccatin III compound represented by formula (B).

The reaction proceeds smoothly at ambient atmosphere and ambient temperature. The process can also be carried out in a dry atmosphere. The process is substantially complete in less than about 5 hours.

The invention also provides a process for synthesizing a C-7 protected 10-deacetylbaccatin III compound represented by formula (C) comprising reacting a 10-deacetylbaccatin III compound represented by formula (B) with a protecting agent in the presence of a secondary amine and a nitrogen-containing compound. The nitrogen-containing compound is selected from a nitrogen-containing heterocycle or a trialkylamine as described more fully below.

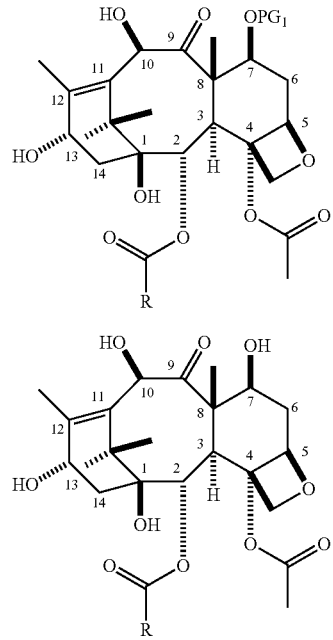

wherein PG$_1$ represents the organic residue of the protecting agent, and R represents a simple or substituted aryl group or a heterocyclic group.

Preferably, the aryl group represented by R is a group represented by the following formula:

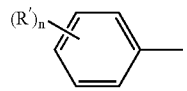

wherein R's may be the same or different and each represents H, an electron withdrawing group or an electron donating group, and n represents 0 or an integer of from 1 to 3. More preferably, the aryl group represented by R is phenyl or substituted phenyl.

Preferably, the electron withdrawing group represented by R' is selected from the group consisting of —F, —NO$_2$, —CN, —Cl, —CHF$_2$ and —CF$_3$, and the electron donating group represented by R' is selected from the group consisting of —NR$_7$R$_8$ and —OR$_9$, wherein R$_7$ and R$_8$ are the same or different and each represents a linear alkyl group having 1 to 10 carbon atoms, a branched or cyclic alkyl group having 3 to 10 carbon atoms, or an unsubstituted or substituted aryl group having 6 to 10 carbon atoms, and R$_9$ represents a linear alkyl group having 1 to 10 carbon atoms, or a branched or cyclic alkyl group having 3 to 10 carbon atoms.

R$_7$ and R$_8$ are preferably the same or different and each represents a linear alkyl group having 1 to 4 carbon atoms, or a branched or cyclic alkyl group having 3 to 4 carbon atoms. It is also preferred that R$_7$ and R$_8$ are the same and represent a linear alkyl group having 1 to 10 carbon atoms, a branched or cyclic alkyl group having 3 to 10 carbon atoms, or an unsubstituted or substituted aryl group having 6 to 10 carbon atoms. Further, more preferably, the substituent —NR$_7$R$_8$ is selected from the group consisting of dimethyl amino, diethyl amino, dipropyl amino and dibutyl amino, wherein the propyl moiety represents normal-propyl or isopropyl, and the butyl moiety represents normal-butyl, secondary butyl, tertiary butyl or isobutyl. More preferably, R' is —OCH$_3$ or a chloro.

The aryl group represented by R is preferably phenyl or substituted phenyl, such as methoxyphenyl, dimethoxyphenyl, or chlorophenyl, and more preferably, represented by the following formulae:

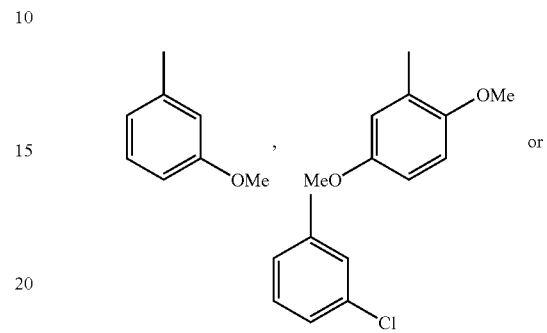

The heterocyclic group represented by R is a 3 to 7 membered ring having 1 to 2 hetero atoms selected from the group consisting of oxygen, nitrogen and sulfur. Examples include furyl, dihydrofuryl, tetrahydrofuryl, pyrollyl, pyrrolidinyl, thienyl, thiazolyl, imidazolyl, pyridyl, morpholinyl, piperidinyl, piperazinyl and oxazolyl. Preferably, the heterocyclic group represented by R is furyl or thienyl. More preferably, the heterocyclic group represented by R is represented by the following formula:

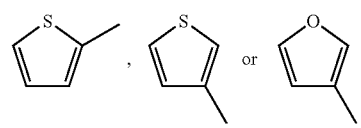

PG$_1$ is preferably trialkylsilyl. More preferably, PG$_1$ is triethylsilyl. The alkyl group is the same or different and is selected from methyl, ethyl, propyl or butyl, wherein the propyl moiety represents normal-propyl or isopropyl, and the butyl moiety represents normal-butyl, secondary butyl, tertiary butyl or isobutyl.

In the present invention, the protecting agent is preferably an organosilane compound and more preferably, an organosilane compound represented by the formula (R")$_3$SiX, wherein R"s may be the same or different, and each independently represents methyl, ethyl, normal-propyl, isopropyl, n-butyl, sec-butyl, isobutyl or tert-butyl, and X represents a leaving group. Preferably, the leaving group represented by X is a halogen atom, tosylate, mesylate, or trifluoromethanesulfonate. Most preferably, the protecting agent is chlorotriethylsilane.

In the present invention, the secondary amine is preferably selected from the group consisting of imidazole and substituted imidazoles, and more preferably imidazole.

In the present invention, the nitrogen-containing compound is preferably anhydrous and selected from a trialkylamine or a nitrogen-containing heterocycle, preferably pyridine.

Examples of suitable trialkylamines include trimethylamine, triethylamine, disopropylethylamine, tri-n-propylamine and tri-n-butylamine.

Examples of suitable nitrogen-containing heterocycles include unsubstituted or substituted pyridine such as 2-picoline, 3-picoline and 4-picoline and unsubstituted or substituted pyrazine, such as methyl pyrazine.

According to the present invention, the amount of the protecting agent is preferably about 2 equivalents based on the amount of the 10-deacetylbaccatin III compound represented by formula (B). The amount of the secondary amine is preferably about 2 to about 6 equivalents based on the amount of the 10-deacetylbaccatin III compound represented by formula (B). The amount of the nitrogen-containing compound is preferably about 0.5 mL per 0.1 g of the 10-deacetylbaccatin III compound represented by formula (B).

The reaction proceeds smoothly at ambient atmosphere and ambient temperature. The process according to the present invention may also be carried out in a dry atmosphere. The process is substantially complete in less than about 20 minutes.

BRIEF DESCRIPTION OF THE DRAWINGS

FIG. 3 depicts the conversion of 10-deacetylbaccatin III compounds (3a–d) into 7-triethylsilylbaccatin III compounds (5a–d).

FIG. 4(a) depicts the synthesis of 7-triethylsilyl-2-debenzoyl-2-(2-thiophenoyl)baccatin III (7) from 2-debenzoyl-2-(2-thiophenoyl)10-deacetyl baccatin III (6).

FIG. 4(b) depicts the synthesis of 7-triethylsilyl-2-debenzoyl-2-(3-furoyl)baccatin III (9) from 2-debenzoyl-2-(3-furoyl)-10-deacetylbaccatin III (8)

FIG. 5 depicts the conversion of 10-deacetylbaccatin III and derivatives (3a–d) to 7-triethylsilyl-10-deacetylbaccatin III and its derivatives (3e–h).

FIG. 6(a) depicts the synthesis of 7-triethylsilyl-2-debenzoyl-2-(2-thiophenoyl)-10-deacetylbaccatin III (7a) from 2-debenzoyl-2-(2-thiophenoyl)-10-deacetylbaccatin III (6a).

FIG. 6(b) depicts the synthesis of 7-triethylsilyl-2-debenzoyl-2-(3-furoyl)-10-deacetylbaccatin III (9a) from 2-debenzoyl-2-(3-furoyl)-10-deacetylbaccatin III (8a)

DETAILED DESCRIPTION OF THE INVENTION

Figure 1:
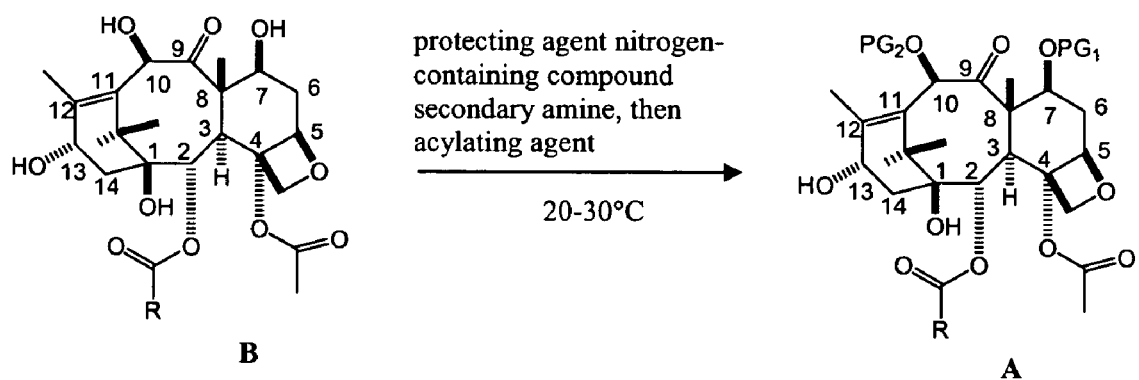
FIG. 1 depicts the conversion of 10-deacetylbaccatin III compounds of formula (B) into C-7 protected baccatin III compounds of formula (A). In the formulae A and B, $PG_1$ represents the organic residue of the protecting agent, $PG_2$ represents the organic residue of the acylating agent, and R represents a simple or substituted aryl group or a heterocyclic group.
Figure 2:
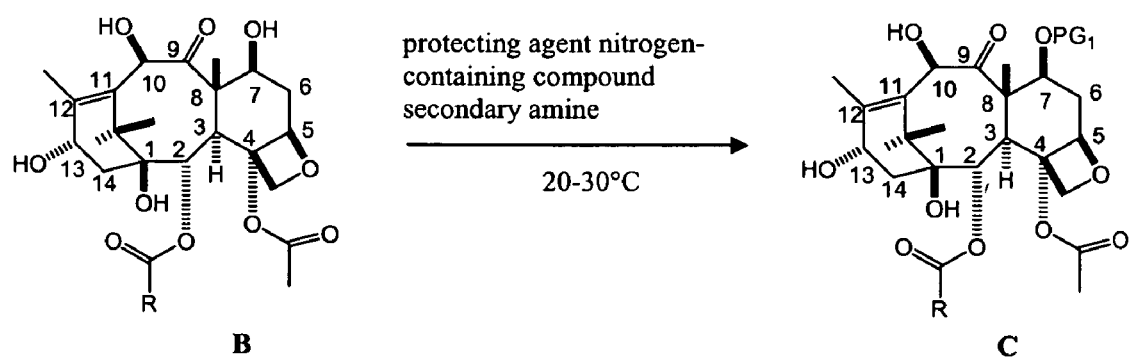
FIG. 2 depicts the conversion of 10-deacetylbaccatin III compounds of formula (B) into C-7 protected 10-deacetylbaccatin III compounds of formula (C). In the formulae B and C, $PG_1$ represents the organic residue of the protecting agent and R represents a simple or substituted aryl group or a heterocyclic group.

The present invention provides a method for the synthesis of a C-7 protected baccatin III compound of formula (A) from a 10-deacetylbaccatin III compound of formula (B) in one step (FIG. 1) without the need for purification of any intermediate. The present invention also provides an improved synthesis of a C-7 protected 10-deacetylbaccatin III compound of formula (C) (FIG. 2). The C-7 protected 10-deacetylbaccatin III compound of formula (C) may in turn be converted to a C-7 protected baccatin III compound represented by formula (A) according to the methods described herein or by the published procedures, such as those described in Denis et al, *J. Am. Chem. Soc.*, 1988, 110, 5917, WO 95/26967 and US 2002/0087013 A1, the disclosures of which are expressly incorporated herein by reference.

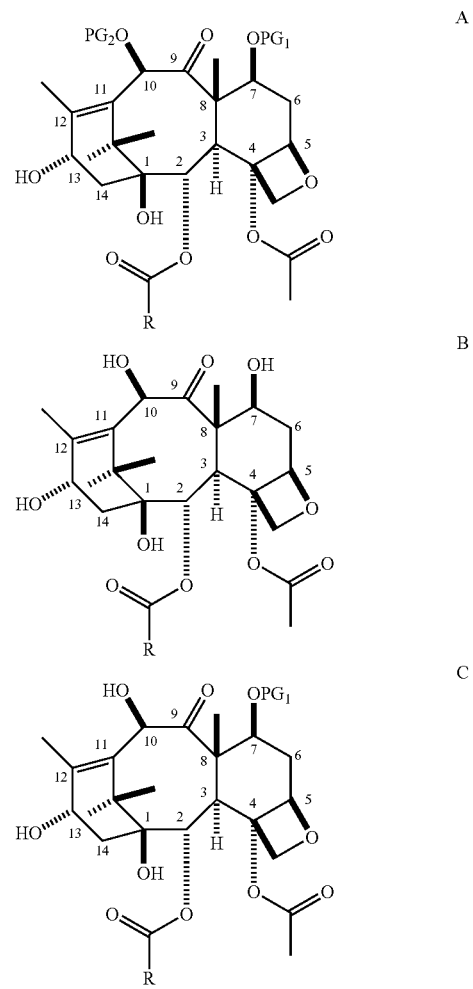

A key feature of this invention is the addition of a secondary amine to the reaction mixture in the presence of a nitrogen-containing compound, which greatly accelerates the reaction. The reaction proceeds in considerably shorter time than any of the previously reported methods, and produces the desired products in high yields. For example, the conversion of a 10-deacetylbaccatin III compound of formula (B) into its 7-protected ether compound of formula (C) is complete in less than about 20 minutes and in quantitative yields. The one-step process for the conversion of a 10-deacetylbaccatin III compound of formula (B) to a C-7 protected baccatin III compound of formula (A) also proceeds in quantitative yields, and is completed in less than 5 hours. However, the reaction can be stirred overnight without formation of an observable amount of side products.

The entire process can be carried out at ambient temperature without the need for cooling or heating. Generally, "ambient temperature" is about 15 to 35° C., preferably about 20 to 30° C., and includes room temperature which is generally about 20–25° C.

The process is readily scalable. The process described herein proceeds smoothly in an ambient atmosphere, e.g., without use of an argon or nitrogen atmosphere. The reaction can also be carried out under a dry atmosphere, such as under an argon or nitrogen atmosphere. One skilled in the art would know, as needed, an appropriate temperature and conditions to carry out the entire process.

In the structural formulae (A), (B) and (C), R represents a simple or substituted aryl group or a heterocyclic group. Examples of the aryl group represented by R include the compounds represented by the following formula:

$(R')_n$—⟨phenyl ring⟩— wherein R's may be the same or different and each represents H, an electron withdrawing group or an electron donating group, and n represents 0 or an integer of from 1 to 3. R is preferably phenyl or substituted phenyl.

Examples of the electron withdrawing group represented by R' include —F, —$NO_2$, —CN, —Cl, —$CHF_2$ and —$CF_3$. Examples of the electron donating group include —$NR_7R_8$ and —$OR_9$, wherein $R_7$ and $R_8$ are the same or different and each represents a linear alkyl group having 1 to 10 carbon atoms, a branched or cyclic alkyl group having 3 to 10 carbon atoms, or an unsubstituted or substituted aryl group having 6 to 10 carbon atoms, and $R_9$ represents a linear alkyl group having 1 to 10 carbon atoms, or a branched or cyclic alkyl group having 3 to 10 carbon atoms. $R_7$ and $R_8$ are also preferably a linear alkyl group having 1 to 4 carbon atoms, or a branched or cyclic alkyl group having 3 to 4 carbon atoms. Preferably, $R_7$ and $R_8$ are the same and represent a linear alkyl group having 1 to 10 carbon atoms, a branched or cyclic alkyl group having 3 to 10 carbon atoms, or an unsubstituted or substituted aryl group having 6 to 10 carbon atoms. Preferred examples of —$NR_7R_8$ include dimethyl amino, diethyl amino, dipropyl amino and dibutyl amino, wherein the propyl moiety represents normal-propyl or isopropyl, and the butyl moiety represents normal-butyl, secondary butyl, tertiary butyl or isobutyl. R' is preferably —$OCH_3$ or chloro.

The aryl group represented by R is preferably phenyl or substituted phenyl, such as methoxyphenyl, dimethoxyphenyl, or chlorophenyl, and more preferably, is represented by the following formulae:

⟨3-methylphenyl with OMe⟩, ⟨methyl, OMe-substituted phenyl with MeO⟩ or ⟨3-chlorophenyl⟩

The heterocyclic group represented by R is a 3 to 7 membered ring having 1 to 2 hetero atoms. Examples of the hetero atoms include oxygen, nitrogen and sulfur. Examples of the heterocyclic group represented by R include furyl, dihydrofuryl, tetrahydrofuryl, pyrollyl, pyrrolidinyl, thienyl, thiazolyl, imidazolyl, pyridyl, morpholinyl, piperidinyl, piperazinyl and oxazolyl. Preferably, the heterocyclic group represented by R is thienyl or furyl, more preferably, 2-thienyl or 3-thienyl, or 3-furyl.

Analogs of 10-deacetylbaccatin III, bearing different C-2 substituents, for example, the compounds represented by formula (B) wherein R is 3-methoxyphenyl, 2,5-dimethoxyphenyl, 3-chlorophenyl, 2-thienyl and 3-furyl may be prepared according to the procedure as previously described in I. Ojima et al, BioOrg. Med. Chem Lett., 9; 3423–3428, 1999, and E. Baloglu et al., BioOrg. Med. Chem., 11; 1557–1568, 2003. The entire disclosures of Ojima, et al. and Baloglu, et al. are expressly incorporated herein by reference. Other analogs may be prepared by an analogous procedure, readily determined by one skilled in the art.

According to the present invention, the process for synthesizing a C-7 protected baccatin III compound represented by formula (A) comprises reacting a 10-deacetylbaccatin III compound represented by formula (B) with a protecting agent and an acylating agent in the presence of a secondary amine and a nitrogen-containing compound selected from a trialkylamine or a nitrogen-containing heterocycle selected from the group consisting of unsubstituted or substituted pyridine and unsubstituted or substituted pyrazine.

A

⟨structure of C-7 protected baccatin III with $PG_2O$, $OPG_1$⟩

B

⟨structure of 10-deacetylbaccatin III with HO, OH⟩ wherein $PG_1$ represents the organic residue of the protecting agent, $PG_2$ represents the organic residue of the acylating agent, and R represents a simple or substituted aryl group or a heterocyclic group.

More specifically, a selected amount of a 10-deacetylbaccatin III compound represented by formula (B) is dissolved in a solvent comprising a nitrogen-containing compound. It is desirable that the nitrogen-containing compound be anhydrous. Next, a secondary amine is introduced to this solution, followed by sequential addition of a protecting agent and an acylating agent. In this method it is preferred that about 0.5 mL of a nitrogen-containing compound is used for every 0.1 g of the 10-deacetylbaccatin III compound represented by formula (B). It is also preferred that about 2 equivalents of the protecting agent are used based on the amount of the 10-deacetylbaccatin III compound represented by formula (B). When less than about 2 equivalents of the protecting agent are used, the C-7 protection might not go to completion. When more than about 2 equivalents of the protecting agent are used, multi-protected products could be observed. The amount of secondary amine is preferably about 2 to about 6 equivalents based on the amount of the 10-deacetylbaccatin III compound represented by formula (B), and the amount of acylating agent is preferably in the range of from about 1 to about 20 equivalents based on the amount of 10-deacetylbaccatin III compound represented by formula (B). It is preferred to use about 6 equivalents of the secondary amine and about 15 equivalents of the acylating agent. The amount of the acylating agent used can be increased to up to about 20 equivalents without formation of side products.

One skilled in the art would know to add, as needed, an appropriate solvent such as tetrahydrofuran, ether, 1,2-dimethoxyethane or dioxane.

The reaction gives excellent yields with a minimum of 95% yield for the triethylsilylation of the C-7 position, and a 90–95% yield for the acylation of the C-10 hydroxyl.

A suitable protecting agent is an organosilane compound. Examples of the protecting agent include organosilane compounds represented by the formula $(R'')_3SiX$, wherein R''s may be the same or different, and each independently represents methyl, ethyl, normal-propyl, isopropyl, n-butyl, sec-butyl, isobutyl or tert-butyl, and X represents a leaving group. Preferably, the leaving group represented by X is a halogen atom, tosylate, mesylate, or trifluoromethanesulfonate. The protecting agent is preferably trialkylsilyl chlorides, trialkylsilyl tosylates, trialkylsilyl mesylates and trialkylsilyl trifluoromethanesulfonates and more preferably chlorotriethylsilane.

Examples of the acylating agent include acyl halides and acyl anhydrides. Preferably, the acylating agent is acetyl chloride or acetic anhydride. More preferably, the acylating agent is acetic anhydride.

$PG_1$ is preferably trialkyllsilyl. The alkyl group is the same or different and is selected from methyl, ethyl, propyl or butyl, wherein the propyl moiety represents normal-propyl or isopropyl, and the butyl moiety represents normal-butyl, secondary butyl, tertiary butyl or isobutyl. $PG_2$ is preferably acyl. More preferably, $PG_1$ is triethylsilyl and $PG_2$ is acetyl.

Examples of the secondary amine include imidazole and substituted imidazoles. Preferably, the secondary amine is imidazole. Based on the teachings herein, one skilled in the art can also use other secondary amines such as unsubstituted or substituted pyrazole, triazole or tetrazole.

Examples of the nitrogen-containing compound include a trialkylamine and a nitrogen-containing heterocycle, such as, unsubstituted or substituted pyridine or unsubstituted or substituted pyrazine.

In the trialkylamine, the alkyl group can be the same or different and is selected from methyl, ethyl, propyl or butyl, where the propyl can be normal-propyl or iso-propyl and the butyl group can be normal-butyl, sec-butyl, tert-butyl or iso-butyl.

Examples of suitable trialkylamines include trimethylamine, triethylamine, diisopropylethylamine, tri-n-propylamine and tri-n-butylamine.

Examples of suitable nitrogen-containing heterocycles include unsubstituted or substituted pyridine such as 2-picoline, 3-picoline and 4-picoline and unsubstituted or substituted pyrazine, such as methyl pyrazine.

Preferably, the nitrogen-containing compound is pyridine.

The present invention also provides a process for synthesizing a C-7 protected 10-deacetylbaccatin III compound represented by formula (C), which comprises reacting a 10-deacetylbaccatin III compound represented by formula (B) with a protecting agent in the presence of a secondary amine and a nitrogen-containing compound selected from a trialkylamine (e.g., triethylamine) or a nitrogen-containing heterocycle selected from the group consisting of unsubstituted and substituted pyridine or unsubstituted or substituted pyrazine,

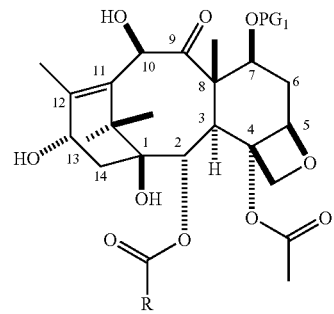

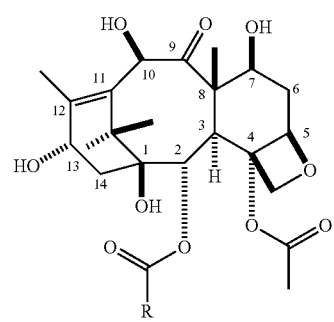

wherein $PG_1$ represents the organic residue of the protecting agent, and R represents a simple or substituted aryl group or a heterocyclic group.

More specifically, a selected amount of a 10-deacetylbaccatin III compound represented by formula (B) is dissolved in a solvent comprising a nitrogen-containing compound. It is desirable that the nitrogen-containing compound be anhydrous. Next, a secondary amine is introduced to this solution, followed by addition of a protecting agent. In this method it is preferred that about 0.5 mL of a nitrogen-containing compound is used for every 0.1 g of the 10-deacetylbaccatin III compound represented by formula (B). It is also preferred that about 2 equivalents of the protecting agent are used based on the amount of the 10-deacetylbaccatin III compound represented by formula (B). When less than about 2 equivalents of the protecting agent are used, the C-7 protection might not go to completion. When more than about 2 equivalents of the protecting agent are used, multi-protected products could be observed. The amount of secondary amine is preferably about 2 to about 6 equivalents based on the amount of the 10-deacetylbaccatin III compound of formula (B). It is also preferred to use about 6 equivalents of the secondary amine.

One skilled in the art would know to add, as needed, an appropriate solvent such as tetrahydrofuran, ether, 1,2-dimethoxyethane or dioxane.

A suitable protecting agent is an organosilane compound. Examples of the protecting agent include organosilane compounds represented by the formula $(R'')_3SiX$, wherein R''s may be the same or different, and each independently represents methyl, ethyl, normal-propyl, isopropyl, n-butyl, sec-butyl, isobutyl or tert-butyl, and X represents a leaving group. Preferably, the leaving group represented by X is a halogen atom, tosylate, mesylate, or trifluoromethanesulfonate. The protecting agent is preferably trialkylsilyl chloride, trialkylsilyltosylate, trialkylsilylmesylate and trialkylsilyltrifluoromethanesulfonate and more preferably chlorotriethylsilane.

Examples of the secondary amine include imidazole and substituted imidazoles. Preferably, the secondary amine is imidazole. Based on the teachings herein, one skilled in the art can also use other secondary amines such as unsubstituted or substituted pyrazole, triazole or tetrazole.

Examples of the nitrogen-containing compound include a trialkylamine and a nitrogen-containing heterocycle, such as, unsubstituted or substituted pyridine or unsubstituted or substituted pyrazine.

In the trialkylamine, the alkyl group can be same or different and is selected from methyl, ethyl, propyl or butyl, where the propyl group can be normal-propyl or iso-propyl and the butyl group can be normal-butyl, sec-butyl, tert-butyl or iso-butyl.

Examples of suitable trialkylamines include trimethylamine, triethylamine, diisopropylethylamine, tri-n-propylamine and tri-n-butylamine.

Examples of suitable nitrogen-containing heterocycles include unsubstituted or substituted pyridine such as 2-picoline, 3-picoline and 4-picoline and unsubstituted or substituted pyrazine, such as methyl pyrazine.

Preferably, the nitrogen-containing compound is pyridine.

The present invention is further described in the following examples. However, the present invention is not limited thereto. Unless otherwise specified, all percents and ratios described herein are by mole based on the amount of the 10-deacetylbaccatin III compound represented by formula (B).

All references cited herein and in the examples that follow are expressly incorporated by references in their entireties.

EXAMPLES

Example 1

Synthesis of 7-triethylsilylbaccatin III (5a, FIG. 3)

10-deacetylbaccatin III (3a) (0.1 g, 0.18 mmol) was dissolved in pyridine (0.5 mL) at about 20 to 25° C. An argon or nitrogen atmosphere was not used. Imidazole (0.074 g, 1.08 mmol) was added to the reaction mixture at about 20 to 25° C., followed by dropwise addition of chlorotriethylsilane (0.06 mL, 0.36 mmol). The reaction mixture was stirred for 5 minutes at about 20 to 25° C., and then treated with acetic anhydride (0.37 mL, 3.9 mmol). The reaction was completed in 4 hours to give the desired product (5a).

Example 2

Synthesis of 7-triethylsilyl-2-debenzoyl-2-(2,5-dimethoxybenzoyl)baccatin III (5b, FIG. 3)

A solution of 2-debenzoyl-2-(2,5-dimethoxybenzoyl)-10-deacetylbaccatin III (3b) (1.50 g, 2.48 mmol) in pyridine (7 mL) was treated with imidazole (0.675 g, 9.93 mmol), followed by chlorotriethylsilane (0.830 mL, 4.97 mmol). The mixture was allowed to stir at about 20 to 25° C., and the progress of the reaction was monitored by TLC (60% ethyl acetate in hexane). After 15 minutes, mono-protection was complete and acetic anhydride (9.2 ml, 97.6 mmol) was introduced into the reaction. The progress of the reaction was then monitored by TLC (30% ethyl acetate in methylene chloride), and found to be complete in 5 hours at about 20 to 25° C. The reaction mixture was diluted with ethyl acetate (40 mL), and washed with water (25 mL), followed by brine (25 mL). The organic layer was dried over anhydrous sodium sulfate, filtered and concentrated in vacuo. The crude product was purified on a silica gel column, using 30% ethyl acetate in methylene chloride as the eluant to afford the desired product (5b) as a white solid (1.25 g, 71% yield): $^1$H NMR (CDCl$_3$) δ 0.55 (m, 6H), 0.91 (t, J=8.0 Hz, 9H), 1.06 (s, 3H), 1.18 (s, 3H), 1.70 (s, 3H), 1.72 (m, 1H), 1.86 (m, 1H), 2.15 (s, 3H), 2.17 (s, 3H), 2.22 (m, 3H), 2.49 (m, 1H), 2.61 (s, 1H), 3.80 (s, 3H), 3.81 (d, J=7.1 Hz, 1H), 3.88 (s, 3H), 4.28 (d, J=8.4 Hz, 1H), 4.31 (d, J=8.4 Hz, 1H), 4.44 (dd, J=6.4, 10.4 Hz, 1H), 4.84 (brt, 1H), 4.91 (d, J=8.6 Hz, 1H), 5.61 (d, J=6.4 Hz, 1H), 6.43 (s, 1H), 6.93 (d, J=9.2 Hz, 1H), 7.06 (dd, J=9.2, 3.2 Hz, 1H), and 7.37 (d, J=3.2 Hz 1H). Mass spectrum: m/z for $C_{39}H_{56}O_{13}SiNa^+$: calcd: 783.35; found: 783.36.

Example 3

Synthesis of 7-triethylsilyl-2-debenzoyl-2-(3-methoxybenzoyl)baccatin III (5d, FIG. 3)

To a solution of 2-debenzoyl-2-(3-methoxybenzoyl)-10-deacetylbaccatin III) (3d, 222 mg, 0.39 mmol) in pyridine (1.5 mL) was added imidazole (105 mg, 1.55 mmol) followed by chlorotriethylsilane (0.129 mL, 0.77 mmol). The reaction mixture was allowed to stir at room temperature, and the progress of the reaction was monitored by TLC analysis (60% ethyl acetate in hexane). After 5 minutes, mono-protection was complete, and acetic anhydride (0.728 mL, 7.73 mmol) was introduced to the reaction. The progress of the reaction was then monitored by TLC (30% ethyl acetate in dichloromethane) and found to be complete in 4 h at room temperature. The reaction mixture was diluted with ethyl acetate (10 mL), washed with water (5 mL) then brine (5 mL) and the organic layer was dried over anhydrous sodium sulfate, and concentrated in vacuo. The crude product was purified by silica gel preparatory TLC using 30% ethyl acetate in dichloromethane (v/v) as the eluant to afford 5d as a white solid (219 mg, 78% yield). $^1$H NMR (CDCl$_3$) δ 0.57 (m, 6H), 0.92 (m, 9H), 1.03 (s, 3H), 1.18 (s, 3H), 1.67 (s, 3H), 1.86 (m, 1H), 2.168 (s, 3H), 2.174 (s, 3H), 2.24 (m, 2H), 2.26 (s, 3H), 2.52 (m, 1H), 3.87 (m, 3H), 4.13 (d, J=8.4 Hz, 1H), 4.33 (d, J=8.4 Hz, 1H), 4.48 (dd, J=6.8, 10.4 Hz, 1H), 4.82 (m, 1H), 4.95 (d, J=8.4 Hz, 1H), 5.61 (d, J=7.2 Hz, 1H), 6.45 (s, 1H), 7.13 (m, 1H), 7.37 (t, J=8.0 Hz, 1H), 7.63 (m, 1H), 7.69 (dd, J=1.2, 8.0 Hz, 1H). $^{13}$C NMR (CDCl$_3$) 5.6, 7.0, 10.2, 15.2, 20.4, 21.2, 23.0, 27.1, 37.6, 38.7, 43.1, 47.6, 55.7, 59.0, 68.2, 72.7, 75.1, 76.1, 76.8, 79.0, 81.2, 84.5, 115.0, 120.3, 122.8, 129.9, 131.0, 132.9, 144.4, 160.0, 167.2, 169.7, 171.0, 202.6. δ m/z MS for $C_{38}H_{54}O_{12}SiNa^+$: calcd: 753.3; found: 753.2.

Example 4

Synthesis of 7-triethylsilyloxy-2-debenzoyl-2-(3-furoyl)baccatin III (9, FIG. 4b)

Chlorotriethylsilane (2 equiv.) was added dropwise to a mixture of 2-debenzoyl-2-(3-furoyl)-10-deacetylbaccati III (8, 1 equiv.) and imidazole (6 equiv.) in pyridine. The reaction mixture was allowed to stir for 10 min at room temperature, after which it was complete. Acetic anhydride (20 equiv.) was added dropwise to the mixture. The reaction mixture was stirred at room temperature. After completion of the reaction, the product was extracted into ethyl acetate, washed sequentially with water, saturated aqueous sodium bicarbonate, water, and brine. The organic layer was separated and dried over sodium sulfate, and concentrated in vacuo. The crude material was purified over silica gel, eluting with 10% ethyl acetate/dichloromethane (v/v) to give the desired product 9. $^1$H NMR (CDCl$_3$) δ0.58 (m, 6H), 0.92 (t, J=8.0 Hz, 9H), 1.04 (s, 3H), 1.17 (s, 3H), 1.64 (s, 1H), 1.66 (s, 3H), 1.87 (m, 1H), 2.10 (d, J=5.2 Hz, 1H), 2.17 (s, 6H), 2.21 (m, 1H), 2.24 (s, 3H), 2.52 (m, 1H), 3.83 (d, J=7.2 Hz, 1H), 4.17 (d, J=8.4 Hz, 1H), 4.38 (d, J=8.4 Hz, 1H), 4.47

(dd, J=6.8, 10.4 Hz, 1H), 4.82 (m, 1H), 4.96 (dd, J=1.6, 9.2 Hz, 1H), 5.51 (d, J=7.2 Hz, 1H), 6.44 (s, 1H), 6.77 (dd, J=0.8, 1.6 Hz, 1H), 7.46 (t, J=1.6 Hz, 1H), 8.07 (dd, J=0.8, 1.6 Hz, 1H). $^{13}$C NMR (CDCl$_3$) δ 5.5, 6.9, 10.1, 15.2, 20.2, 21.1, 22.9, 27.0, 37.4, 38.3, 42.9, 47.4, 58.8, 68.1, 72.5, 74.3, 75.9, 76.8, 78.9, 81.1, 84.4, 110.0, 119.2, 132.8, 144.1, 144.3, 148.8, 163.7, 169.6, 170.9, 202.3. m/z MS for $C_{35}H_{50}O_{12}SiNa^+$: calcd: 713.3; found: 713.1

I claim:

1. A process for synthesizing a compound represented by formula (A), which comprises reacting a 10-deacetylbaccatin III compound represented by formula (B) with a protecting agent in the presence of a secondary amine and a nitrogen-containing compound selected from a trialkylamine or a nitrogen-containing heterocycle selected from the group consisting of unsubstituted or substituted pyridine and unsubstituted or substituted pyrazine, and then with an acylating agent,

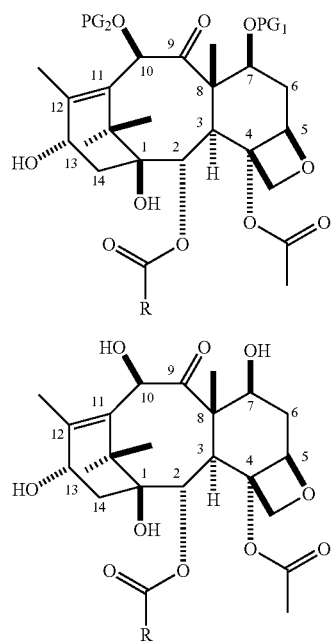

wherein PG$_1$ represents the organic residue of the protecting agent, PG$_2$ represents the organic residue of the acylating agent, and R represents a simple or substituted aryl group or a heterocyclic group.

2. The process according to claim 1, wherein the aryl group is a group represented by the following formula:

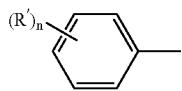

wherein R's may be the same or different and each represents H, an electron withdrawing group or an electron donating group, and n represents 0 or an integer of from 1 to 3.

3. The process according to claim 1, wherein the aryl group represented by R is phenyl or substituted phenyl.

4. The process according to claim 2, wherein the electron withdrawing group is selected from the group consisting of —F, —NO$_2$, —CN, —Cl, —CHF$_2$ and —CF$_3$.

5. The process according to claim 2, wherein the electron donating group is selected from the group consisting of —NR$_7$R$_8$ and —OR$_9$, wherein R$_7$ and R$_8$ are the same or different and each represents a linear alkyl group having 1 to 10 carbon atoms, a branched or cyclic alkyl group having 3 to 10 carbon atoms, or an unsubstituted or substituted aryl group having 6 to 10 carbon atoms, and R$_9$ represents a linear alkyl group having 1 to 10 carbon atoms, or a branched or cyclic alkyl group having 3 to 10 carbon atoms.

6. The process according to claim 2, wherein R' represents —OCH$_3$ or chloro.

7. The process according to claim 1, wherein the aryl group represented by R is selected from the group consisting of methoxyphenyl, dimethoxyphenyl and chlorophenyl.

8. The process according to claim 1, wherein the aryl group represented by R is selected from the group consisting of the following formulae:

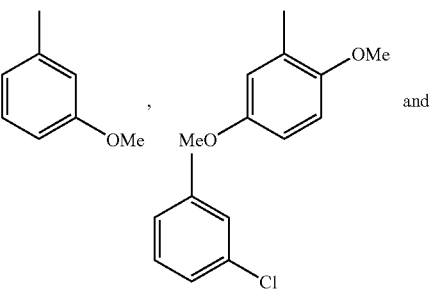

9. The process according to claim 5, wherein R$_7$ and R$_8$ are the same or different and each represents a linear alkyl group having 1 to 4 carbon atoms, or a branched or cyclic alkyl group having 3 to 4 carbon atoms.

10. The process according to claim 5, wherein R$_7$ and R$_8$ are the same and represent a linear alkyl group having 1 to 10 carbon atoms, a branched or cyclic alkyl group having 3 to 10 carbon atoms, or an unsubstituted or substituted aryl group having 6 to 10 carbon atoms.

11. The process according to claim 5, wherein —NR$_7$R$_8$ is selected from the group consisting of dimethyl amino, diethyl amino, dipropyl amino and dibutyl amino, wherein the propyl moiety represents normal-propyl or isopropyl, and the butyl moiety represents normal-butyl, secondary butyl, tertiary butyl or isobutyl.

12. The process according to claim 1, wherein the heterocyclic group represented by R is a 3 to 7 membered ring having 1 to 2 hetero atoms selected from the group consisting of oxygen, nitrogen and sulfur.

13. The process according to claim 1, wherein the heterocyclic group represented by R is selected from the group consisting of furyl, dihydrofuryl, tetrahydrofuryl, pyrollyl, pyrrolidinyl, thienyl, thiazolyl, imidazolyl, pyridyl, morpholinyl, piperidinyl, piperazinyl and oxazolyl.

14. The process according to claim 1, wherein the heterocyclic group represented by R is selected from thienyl or furyl.

15. The process according to claim 1, wherein the heterocyclic group represented by R is selected from the following formulae:

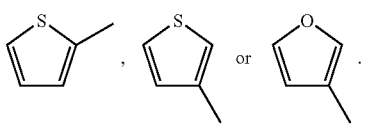

16. The process according to claim 1, wherein PG$_1$ is trialkylsilyl.

17. The process according to claim 1, wherein PG$_2$ is acyl.

18. The process according to claim 16 or 17, wherein PG$_1$ is triethylsilyl and PG$_2$ is acetyl.

19. The process according to claim 1, wherein the protecting agent is an organosilane compound.

20. The process according to claim 1, wherein the protecting agent is an organosilane compound represented by the formula (R″)$_3$ SiX, wherein R″s may be the same or different, and each independently represents methyl, ethyl, normal-propyl, isopropyl or tert-butyl, and X represents a leaving group.

21. The process according to claim 20, wherein the leaving group represented by X is selected from the group consisting of a halogen atom, tosylate, mesylate, and trifluoromethanesulfonate.

22. The process according to claim 1, wherein the protecting agent is chlorotriethylsilane.

23. The process according to claim 1, wherein the acylating agent is selected from the group consisting of acyl halides and acyl anhydrides.

24. The process according to claim 1, wherein the acylating agent is selected from the group consisting of acetyl chloride and acetic anhydride.

25. The process according to claim 24, wherein the acylating agent is acetic anhydride.

26. The process according to claim 1, wherein the secondary amine is a substituted imidazole.

27. The process according to claim 1, wherein the secondary amine is imidazole.

28. The process according to claim 1, wherein the nitrogen-containing compound is a nitrogen-containing heterocycle selected from the group consisting of pyridine, 2-picoline, 3-picoline, 4-picoline, pyrazine and methylpyrazine or a trialkylamine selected from the group consisting of trimethylamine, triethylamine, diisopropylethylamine, tri-n-propylamine, and tri-n-butylamine.

29. The process according to claim 1, wherein the nitrogen-containing compound is pyridine or triethylamine.

30. The process according to claim 1, wherein the nitrogen-containing compound is anhydrous.

31. The process according to claim 1, wherein the amount of the protecting agent is about 2 equivalents based on the amount of the 10-deacetylbaccatin III compound represented by formula (B).

32. The process according to claim 1, wherein the amount of the acylating agent is in a range of from about 1 to about 20 equivalents based on the amount of the 10-deacetylbaccatin III compound represented by formula (B).

33. The process according to claim 1, wherein the amount of the secondary amine is about 2 to about 6 equivalents based on the amount of the 10-deacetylbaccatin III compound represented by formula (B).

34. The process according to claim 1, wherein the amount of the nitrogen-containing compound is about about 0.5 mL per 0.1 g of the 10-deacetylbaccatin III compound represented by formula (B).

35. The process according to claim 1, wherein the process is carried out at ambient temperature.

36. The process according to claim 1, wherein the process is carried out in a dry atmosphere.

37. The process according to claim 1, wherein the process is carried out at ambient atmosphere.

38. The process according to claim 1, wherein the process is substantially complete in less than about 5 hours.

39. A process for synthesizing a compound represented by formula (C), which comprises reacting a 10-deacetylbaccatin III compound represented by formula (B) with a protecting agent in the presence of a secondary amine and a nitrogen-containing compound selected from a trialkylamine or a nitrogen-containing heterocycle selected from the group consisting of unsubstituted or substituted pyridine and unsubstituted or substituted pyrazine,

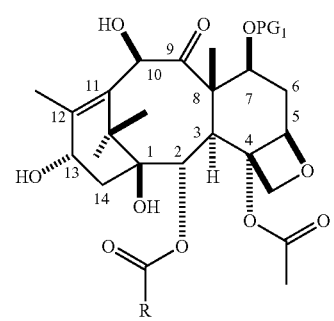

C

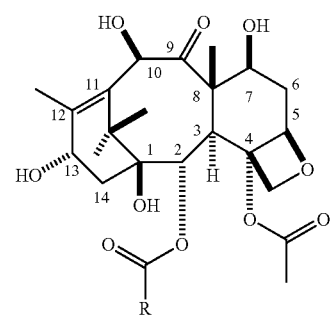

B wherein PG$_1$ represents the organic residue of the protecting agent, and R represents a simple or substituted aryl group or a heterocyclic group.

40. The process according to claim 39, wherein the aryl group represented by R is a group represented by the following formula:

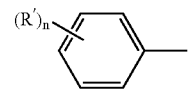

wherein R's may be the same or different and each represents H, an electron withdrawing group or an electron donating group, and n represents 0 or an integer of from 1 to 3.

41. The process according to claim 39, wherein the aryl group represented by R is phenyl or substituted phenyl.

42. The process according to claim 40, wherein the electron withdrawing group is selected from the group consisting of —F, —NO$_2$, —CN, —Cl, —CHF$_2$ and —CF$_3$.

43. The process according to claim 40, wherein the electron donating group is selected from the group consisting of —$NR_7R_8$ and —$OR_9$, wherein $R_7$ and $R_8$ are the same or different and each represents a linear alkyl group having 1 to 10 carbon atoms, a branched or cyclic alkyl group having 3 to 10 carbon atoms, or an unsubstituted or substituted aryl group having 6 to 10 carbon atoms, and $R_9$ represents a linear alkyl group having 1 to 10 carbon atoms, or a branched or cyclic alkyl group having 3 to 10 carbon atoms.

44. The process according to claim 40, wherein R' represents —$OCH_3$ or chloro.

45. The process according to claim 39, wherein the aryl group represented by R is selected from the group consisting of methoxyphenyl, dimethoxyphenyl and chlorophenyl.

46. The process according to claim 39, wherein the aryl group represented by R is selected from the group consisting of the following formulae:

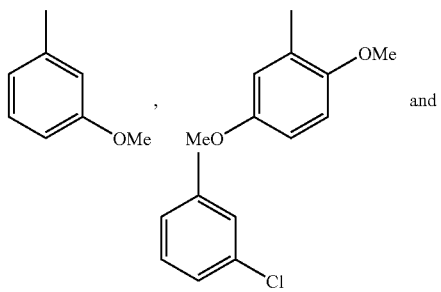

47. The process according to claim 43, wherein $R_7$ and $R_8$ are the same or different and each represents a linear alkyl group having 1 to 4 carbon atoms, or a branched or cyclic alkyl group having 3 to 4 carbon atoms.

48. The process according to claim 43, wherein $R_7$ and $R_8$ are the same and represent a linear alkyl group having 1 to 10 carbon atoms, a branched or cyclic alkyl group having 3 to 10 carbon atoms, or an unsubstituted or substituted aryl group having 6 to 10 carbon atoms.

49. The process according to claim 43, wherein the —$NR_7R_8$ is selected from the group consisting of dimethyl amino, diethyl amino, dipropyl amino and dibutyl amino, wherein the propyl moiety represents normal-propyl or isopropyl, and the butyl moiety represents normal-butyl, secondary butyl, tertiary butyl or isobutyl.

50. The process according to claim 39, wherein the heterocyclic group represented by R is a 3 to 7 membered ring having 1 to 2 hetero atoms selected from the group consisting of oxygen, nitrogen and sulfur.

51. The process according to claim 39, wherein the heterocyclic group represented by R is selected from the group consisting of furyl, dihydrofuryl, tetrahydrofuryl, pyrollyl, pyrrolidinyl, thienyl, thiazolyl, imidazolyl, pyridyl, morpholinyl, piperidinyl, piperazinyl and oxazolyl.

52. The process according to claim 39, wherein the heterocyclic group represented by R is thienyl or furyl.

53. The process according to claim 39, wherein the heterocyclic group represented by R is selected from the following formula:

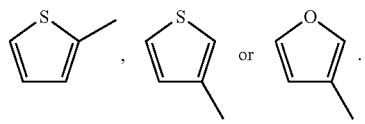

54. The process according to claim 39, wherein $PG_1$ is trialkylsilyl.

55. The process according to claim 39, wherein the protecting agent is an organosilane compound.

56. The process according to claim 39, wherein the protecting agent is an organosilane compound represented by the formula $(R'')_3$ SiX, wherein R''s may be same or different, and each independently represents methyl, ethyl, normal-propyl, isopropyl or tert-butyl, and X represents a leaving group.

57. The process according to claim 56, wherein the leaving group represented by X is selected from the group consisting of a halogen atom, tosylate, mesylate, and trifluoromethanesulfonate.

58. The process according to claim 39, wherein the protecting agent is chlorotriethylsilane.

59. The process according to claim 39, wherein the secondary amine is a substituted imidazole.

60. The process according to claim 39, wherein the secondary amine is imidazole.

61. The process according to claim 39, wherein the nitrogen-containing compound is a nitrogen-containing heterocycle selected from the group consisting of pyridine, 2-picoline, 3-picoline, 4-picoline, pyrazine and methylpyrazine or a trialkylamine selected from the group consisting of trimethylamine, triethylamine, diisopropylethylamine, tri-n-propylamine, and tri-n-butylamine.

62. The process according to claim 39, wherein the nitrogen-containing compound is pyridine or triethylamine.

63. The process according to claim 39, wherein the nitrogen-containing compound is anhydrous.

64. The process according to claim 39, wherein the process is carried out at ambient temperature.

65. The process according to claim 39, wherein the process is carried out in a dry atmosphere.

66. The process according to claim 39, wherein the process is carried out at ambient atmosphere.

67. The process according to claim 39, wherein the process is substantially complete in less than about 20 minutes.

68. The process according to claim 39, wherein the amount of the protecting agent is about 2 equivalents based on the amount of the 10-deacetylbaccatin III compound represented by formula (B).

69. The process according to claim 39, wherein the amount of the secondary amine is about 2 to about 6 equivalents based on the amount of the 10-deacetylbaccatin III compound represented by formula (B).

* * * * *